United States Patent [19]

Conrad et al.

[11] Patent Number: 5,250,519
[45] Date of Patent: Oct. 5, 1993

[54] NON-ANTICOAGULANT HEPARIN DERIVATIVES

[75] Inventors: H. Edward Conrad; Yuchuan Guo, both of Alameda, Calif.

[73] Assignee: Glycomed Incorporated, Alameda, Calif.

[21] Appl. No.: 677,737

[22] Filed: Mar. 29, 1991

[51] Int. Cl.$^5$ .................... A61K 31/725; C08B 37/10
[52] U.S. Cl. ........................ 514/56; 514/54; 536/21; 536/53; 536/55.3; 536/124
[58] Field of Search ............... 514/54, 56; 536/21, 536/55.3, 124, 53

[56] References Cited

U.S. PATENT DOCUMENTS

| | | | |
|---|---|---|---|
| 4,816,446 | 3/1989 | Feller et al. | 536/21 |
| 4,981,955 | 1/1991 | Lopez | 536/21 |
| 5,032,679 | 7/1991 | Brandley et al. | 536/21 |
| 5,104,860 | 4/1992 | Piani et al. | 514/56 |
| 5,116,962 | 5/1992 | Stüber et al. | 536/21 |

OTHER PUBLICATIONS

Mcall's *Dictionary of Chemistry* Sharp (Ed.) (1981) p. 251.
Nagasawa et al; *J. Biochem*, 81:989–993 (1977).
Hoover et al; *Circ. Res.* 47(4):578–583 (1980).
Nagasawa et al; *Carb. Res.* 111:273–281 (1983).
Shaklee et al; *Biochem. J.* 217:187–197 (1984).
Oasu et al; *Chemical Abstracts* 112:120980x (1990).
Austin et al., *J. Am. Coll. Cardiol.* (1985) 6:369–375.
Guo et al., *Anal. Biochem.* (1988) 268:54–62.
Clowes et al., *Nature* (1977) 265:625–626.
Marcum et al., *Biology of Proteoglycan*, Academic Press (1987) pp. 301–343.
Castellot, Jr., et al., *J. Biol. Chem.* (1982) 257:11256–11260.
Benitz et al. *J. Cell. Physiol.* (1966) 127:1–7.
Orlidge et al., *Microvascular Res.* (1986) 31:41–53.
Benitz et al., *The Pulmonary Circulation: Normal and Abnormal*, Fishman, A. P., ed., University of Pennsylvania Press, (1988) 30 pages.
Castellot, Jr. et al., *J. Cell. Physiol* (1984) 120:315–320.
Castellot, Jr., et al, *J. Cell. Biol.* (1986) 102:1979–1984.
Barzu et al. *J. Cell Physiol.* (1989) 140:538–548.
Wright et al., *J. Biol. Chem.* (1989) 264:1534–1542.
Fransson et al., *FEBS Letters* (1979) 97:119–123.
Casu et al., *Arzneim Forch/Drug Res.* (1986) 36:637–642.
Fransson et al., *Carbohydrate Res.* (1980) 80:131–145.
Bjornsson et al., *J. Pharmacol. & Exper. Therap.* (1988) 245(3):804–808.
Edge et al., *Arch. Biochem. & Biophys.* (1985) 240(2):560–572.

*Primary Examiner*—Nancy S. Husarik
*Attorney, Agent, or Firm*—Gregory J. Giotta

[57] ABSTRACT

A non-anticoagulant (NAC) form of heparin which shows antiproliferative activity with respect to smooth muscle cells is useful in the prevention of restenosis and other conditions benefited by antiproliferative activity with respect to smooth muscle cells. This NAC form of heparin is prepared by deacetylating and then oxidizing heparin/heparan sulfate substantially to completion with periodate followed by reduction of the resulting aldehyde groups under conditions which prevent depolymerization of the heparin.

10 Claims, No Drawings

NON-ANTICOAGULANT HEPARIN DERIVATIVES

TECHNICAL FIELD

The invention relates to heparin-derived pharmaceutical compositions which are useful as antiproliferative agents but lack anticoagulant activity. More particularly, the invention concerns substantially full-length heparin oligomers which have been depleted of anticoagulant activity but not antiproliferative activity by oxidation with periodate and reduction of the resulting aldehydes under conditions which minimize fragmentation of the heparin.

ABBREVIATIONS

The following abbreviations are used for monosaccharides or for monosaccharide residues included in oligomers: D-glucuronic acid = GlcA; L-iduronic acid = IdoA; D-glucosamine = GlcNH$_2$; N-acetyl-D-glucosamine = GlcNAc; D-glucosamine N-sulfate = GlcNS; 2,5-anhydromannose = AMan; 2,5-anhydromannitol = AManH.

The location of the O-linked sulfate residues is indicated by "S" and the number of the position of sulfation where the sulfate residue is linked to oxygen on the sugar residue. In the designations for heparin structure, also, the alpha and beta anomeric linkages are as those conventionally found in heparin and the indicated D or L configurations as conventionally found pertains. The locations of the sulfates are shown below the abbreviation for the sugar to which they apply, thus, for example,

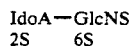

refers to a dimer of L-iduronic acid and D-glucosamine N-sulfate with sulfates connected respectively at the 2 and 6 positions of the sugar residues.

BACKGROUND ART

Proliferation of smooth muscle cells in blood vessel walls occurs in response to vascular injury, and in association with certain disease states (Austin, G.E., et al., *J Am Coll Cardiol* (1985) 6:369-375). The proliferation of these cells can have negative effects due to the production of excess proteins or other matrix molecules, which, along with the cells themselves, form pathologic lesions of, for example, atherosclerosis, renal hypertension, pulmonary hypertension, vasculitis, and post-surgical vascular restinosis. These results are distinguished from the acute response to trauma characterized by blood clotting.

Heparin/heparan sulfate is known to inhibit smooth muscle cell proliferation. Heparin/heparan sulfate is a member of a class known as glycosaminoglycans (GAG). These materials are copolymers of alternating hexosamine and aldouronic acid residues which are found in sulfated forms and are synthesized as proteoglycans.

In the compositions of interest herein, heparan sulfate and heparin, the hexosamine is mostly N-acetylated or N-sulfated glucosamine (GlcNH$_2$), and the aldouronic acid is mostly L-iduronic in heparin and mostly D-glucuronic acid in heparan sulfate. Heparan sulfate is commonly considered to have a higher proportion of glucuronic acid than heparin.

Problems of heterogeneity in preparations of heparan sulfate or heparin isolated from tissues make sharp distinctions difficult, since these oligosaccharides are related by the biosynthesis pathway, as explained below. Conventional heparin (used as an anticoagulant) has a molecular weight of 5-25 kDa and is extracted as a mixture of various chain lengths by conventional procedures. These procedures involve autolysis and extraction of suitable tissues, such as beef or porcine lung, intestine, or liver, and removal of nonpolysaccharide components.

The molecular weight of the chains in the extract is significantly lower than the 60-100 kd known to exist in the polysaccharide chains of the heparin proteoglycan synthesized in the tissue. The GAG moiety is synthesized bound to a peptide matrix at a serine residue through a tetrasaccharide linkage region of the sequence D-GlcA-D-Gal-D-Gal-D-Xyl → protein, which is then elongated at the D-GlcA residue with alternate additions of GlcNAc and GlcA.

The polysaccharide side chains are modified by a series of enzymes which sequentially deacetylate the N-acetyl glucosamine and replace the acetyl group with sulfate, epimerize the hydroxyl at C5 of the D-glucuronic acid residue (to convert it to L-iduronic acid and the GAG chain from the heparan type to a heparin type), sulfate the O-2 of the resulting L-iduronic acid and the O-6 of the glucosamine residue. Some of the chains are further sulfated at the O-3 of the glucosamine residue, either at the heparan or heparin stage. This further sulfation is associated with the active site for antithrombin (anticlotting) activity. Other chemically possible sulfation sites are on the 0-3 of L-iduronic or D-glucuronic and 0-2 of D-glucuronic acid; however, these are seldom found.

Due to their obvious chemical similarity, isolated "heparin" may contain considerable amounts of what might otherwise be classified as heparan sulfate.

There is an extensive body of art concerning depolymerization of heparin/heparan sulfate chains and separation of products by size. Particularly relevant is the report of Guo, Y., et al., *Anal Biochem* (1988) 168:54-62 which discloses the results of structure determination after the 2,5-anhydromannose at the reducing terminus is reduced to the corresponding 2,5-anhydromannitol.

The involvement of heparin or heparan sulfate or degradation products thereof in smooth muscle proliferation has been recognized for some time. Heparin and heparan sulfate can slow or arrest the vascular proliferation associated with injury described hereinabove (Clowes, A. W., et al., *Nature* (1977) 265:625-626). The effect of heparan sulfate and heparin on smooth muscle proliferation is also described by Marcum, J. A., et al. in *Biology of Proteoglycan,* Academic Press (1987) pp. 130-343. The inhibition of vascular smooth muscle cell growth by heparin was further described by Castellot, J. J., Jr., et al., *J Biol Chem* (1982) 257:11256-11260, and the effect of heparin on vascular smooth muscle cell growth in fetal tissue was described by Benitz, W. E., et al., *J Cell Physiol* (1986) 127:1-7. The effect of heparin as an inhibitor of both pericyte and smooth muscle cell proliferation was shown by Orlidge, A., et al., *Microvascular Research* (1986) 31:41-53, and these authors further showed that chondroitin sulfate, and dermatan sulfate do not have this effect. A review of the effects of heparin and heparan sulfate on the proliferation of smooth muscle cells has been published by Benitz, W. E. in "The Pulmonary Circulation: Normal and Abnormal", Fishman, A. P., ed., University of Pennsylvania Press (1988).

It is not clear by what mechanism these glycosaminoglycans operate, or to what extent they interact with other growth factors such as epithelial and fibroblast growth factors. It has been proposed that a 3-O sulfate on glucosamine in an oligosaccharide of at least 5 sugars is important in this process and that both O- and N-sulfation is important (Castellot, J. J., et al., *J Cell Physiol* (1984) 120:315-320; Castellot, J. J., et al., *J Cell Biol* (1986) 102:1979-1984). Hexasaccharides-decasaccharides obtained from partial nitrous acid digestion of heparin bind to acidic fibroblast growth factor and aid its mitogenic activity in fibroblasts, but inhibit the proliferation of endothelial cells under some conditions (Barzu, T., et al., *J Cell Physiol* (1989) 140:538-548). The effective hexasaccharide was stated to have the structure:

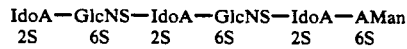

Others have indicated that the presence of 2-0-sulfate glucuronic acid is not necessary for antiproliferative activity (Wright, Jr., T. C., et al., *J Biol Chem* (1989) 264:1534-1542). In this article, size separated fragments of defined length prepared by nitrous acid cleavage and gel filtration were further separated according to charge for some assays. Partially digested heparin separated only according to size was tested with respect to stimulation of smooth muscle cells and epithelial cells. Similar results were found in both cases, although the results were not identical. Tetrasaccharides of the type tested were shown to have very low antiproliferative activity; hexasaccharides, octasaccharides and decasaccharides were shown to be active to approximately the same level on a weight/volume concentration basis. Also tested was a synthetic pentasaccharide which represents a unique sequence of the heparin-binding site in heparin to antithrombin III; this polysaccharide was active in inhibiting proliferation for smooth muscle cells, but not for epithelial cells.

The size separated fractions were then treated chemically to produce "O-oversulfation" and this treatment enhanced the inhibitory activity; indeed, 0-oversulfation of the tetrasaccharide fragment preparation caused the tetrasaccharide fraction to become active in inhibiting proliferation. The converse process, comprising desulfation and reacetylation of the amino groups or glucosamine results in a reduction in antiproliferative activity. These fragments could, however, be made more active by subsequent O-oversulfation.

Also capable of reducing the antiproliferative activity of the heparin fragments was reduction of the carboxyl groups so as to reduce the total negative charge. O-oversulfation partially, at least, restores this activity. These results with N-desulfated, N-acetylated fragments which are lacking in antiproliferative activity is distinguishable from previous results wherein similarly treated heparin retains the capacity to prevent cell division because of the size dependency of the antiproliferative activity-larger fragments being more powerful in general than smaller ones.

Finally, when the size separated fraction was then further fractionated according to charge, it was found that the most highly charged fractions showed the greatest activity. Furthermore, it was shown that although the synthetic pentasaccharide identified with the antithrombin III binding site is capable of inhibiting proliferation in smooth muscle cells, treatment of heparin which would destroy the sequence corresponding to this pentasaccharide (i.e., periodate treatment) does not destroy antiproliferative activity. This pentasaccharide has the structure:

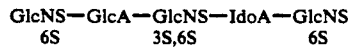

Treatment of heparin/heparan sulfate with periodate has also been reported by others. Fransson and Lewis, *FEBS Lett* (1979) 97:119-123, describe a variety of conditions relating to the treatment of heparin/heparan sulfate with periodate and reduction by sodium borohydride or fragmentation in alkaline medium. Casu et al., *Arzneim Forsch/Drug Res* (1986) 36:637-642, report treatment of heparin with periodate followed by partial acid hydrolysis which results in fragmentation of the chains and partial destruction of the functional groups, as noted by Fransson (*Carbohydrate Res* (1980) 80:131-145). In all of these processes, the periodate treatment itself and/or subsequent procedures resulted in fragmentation of the heparin chain.

It will be noted that heparin is a complex molecule with a complex array of activities in vivo. While a particular subunit, specifically a pentasaccharide, has tentatively been designated as responsible for anticoagulant activity, heparin is also known to bind to a variety of growth factors to mediate or inhibit growth of various cell types, and may provide additional functions as yet to be ascertained. The overall structure of the molecule may be important in some degree in some or all of these. Also, the polymers generally are expected to have multiple binding sites which results in a bonding affinity not generated by a smaller fragment. Thus there is advantage in maintaining the integrity of the heparin molecule to the extent possible when destroying undesirable functions, i.e., anticoagulation properties.

The present invention provides inactivation of the anticoagulant ability of heparin without destruction of antiproliferative activity without fragmentation of the heparin chains, thus preserving to the extent possible desirable additional functions. This process has the additional advantage of retaining the size distribution of the naturally-occurring heparin/heparan sulfate preparation, which results in a therapeutic having a more readily recognized physiological profile.

DISCLOSURE OF THE INVENTION

The invention provides processes for obtaining non-anticoagulant (NAC) heparin preparations which exhibit useful antiproliferative activity and which largely retain the size characteristics of naturally-occurring heparin. The invention process comprises first deacetylating with hydrazine and then treating the heparin/heparan sulfate with periodate under conditions to effect complete conversion of gem-diols and gem alcohol-free amines to aldehydes followed by reduction of the aldehyde moieties under conditions wherein fragmentation is minimized. As the heparin/heparan sulfate is treated first with a reagent to deacetylate any GlcNAc residues in the preparation, this renders the resulting glucosamine susceptible to periodate oxidation at the C2—C3 bond provided the oxygen at position 3 is not sulfated.

In one aspect, the invention is directed to a process to prepare NAC-heparin which comprises removing substantially all acetyl derivatizing moieties from the GlcNAc residues in the oligomer followed by treating the deacetylated heparin/heparan sulfate with periodate under conditions which result in the conversion of all gemdiols or gem-OH/NH$_2$ to the corresponding aldehydes, followed by reduction of the aldehydes to alcohol moieties under conditions which cause little fragmentation of the oligomer.

In another aspect, the invention is directed to the antiproliferative NAC-heparin which results from the foregoing process, and to pharmaceutical compositions having the NAC heparin as active ingredient. Such compositions may be administered to a patient in order to regulate smooth muscle cell proliferation. In still another aspect, the invention is directed to methods to treat conditions benefited by preventing smooth muscle cell proliferation using the NAC-heparin of the invention.

MODES OF CARRYING OUT THE INVENTION

The starting material for the NAC-antiproliferative heparin derivative of the invention is commercially available heparin/heparan sulfate.

By "heparin/heparan sulfate" or "heparin" is meant a preparation obtained from tissues in a manner conventional for the preparation of heparin as an anticoagulant or otherwise synthesized and corresponding to that obtained from tissue. See Conrad, H. E., *Heparin and Related Polysaccharides*, Vol. 56, p. 18 of Annals of N.Y., Academy of Sc., Jun. 7, 1989, incorporated herein by reference. This preparation may include residues of D-glucuronic acid (GlcA), as characteristic of heparan sulfate as well as iduronic acid (IdoA) as characteristic of heparin. However, both GlcA and IdoA are present in both, they are present in different proportional amounts. The (IdoA)/GlcA ratio rises as heparan sulfate becomes more heparin-like. As described in the Background section above, the conversion of D-glucuronic acid to L-iduronic acid is a result of epimerization at the 5 carbon of GlcA residues in a heparan-type intermediate. This sequence of steps involved in such epimerization and conversion is understood in the art. To the extent that full conversion has not been made, heparan sulfate characteristics remain in the preparation. Because the precise nature of the polymeric chains in the preparations of heparin is not generally determined, and varies from preparation to preparation, the term "heparin/heparan sulfate" or "heparin" is intended to cover the range of mixtures encountered. Perhaps the main feature which distinguishes heparan sulfate from heparin is that the latter has anti-coagulant activity.

The "heparin/heparan sulfate" preparation can be obtained from a variety of mammalian tissues, including, if desired, human tissue. Generally, porcine or bovine sources are used, and vascularized tissues are preferred. A preferred source of heparin/heparan sulfate starting material is porcine intestinal mucosa, and preparations labeled "heparin" prepared from this tissue source are commercially available. In general, the heparin/heparan sulfate starting material is prepared from the selected tissue source by allowing the tissue to undergo autolysis and extracting the tissue with alkali, followed by coagulation of the protein, and then precipitation of the heparin-protein complex from the supernatant by acidification. The complex is recovered by reprecipitation with a polar nonaqueous solvent, such as ethanol or acetone or their mixtures, and the fats are removed by extraction with an organic solvent such as ethanol and proteins by treatment with a proteolytic enzyme, such as trypsin. Suitable procedures for the preparation of the heparin starting material are found, for example, in Charles, A. F., et al., *Biochem J* (1936) 30:1927-1933, and modifications of this basic procedure are also known, such as those disclosed by Coyne, E., in *Chemistry and Biology of Heparin*, Elsevier Publishers, North Holland, New York, Lunblad, R.L., et al., eds. (1981).

By "NAC-antiproliferative heparin" is meant the product of the invention process which is a mixture of minimally-fragmented heparin chains which have been deacetylated, oxidized by periodate and then reduced. The mixture has antiproliferative activity but lacks substantial anticoagulant activity. Thus, the invention composition is an minimally-fragmented heparin/heparan sulfate derivative mixture which has been deacetylated to liberate gem OH/NH$_2$ groups susceptible to periodate, oxidized by periodate and reduced without fragmentation of the polymers. The range of molecular weights is that typical for commercial heparin preparations—i.e., 5-25 kd. It is estimated that the majority of the composition comprises glycosaminoglycan chains of 10-20 kd. This corresponds to approximately 50-100 saccharide units.

In general, the heparin/heparan sulfate is treated with periodate under conditions wherein all of the gem-diols or gem OH/NH$_2$ contained in the glycosaminoglycan structure are oxidized to the corresponding aldehydes. Thus, all of the idouronic acid or glucuronic acid residues which contain neither 2-sulfate nor 3-sulfate would be oxidized. Glucosamine residues containing free amino groups freed by deacetylation will also be oxidized; glucosamine residues which are N-sulfated are unaffected.

The periodate oxidation is then followed by reduction of the resulting aldehydes to alcohols under conditions wherein fragmentation of the glycosaminoglycan polymer does not take place. The resultant nonanticoagulant (NAC) heparin derivative retains antiproliferative activity vis-á-vis smooth muscle cells.

In general, the deacetylation step is conducted by dissolving the heparin/heparan sulfate in about 70% aqueous hydrazine (v/v) containing about 1% hydrazine sulfate. The heparin concentration is in the range of 0.2-10% (w/v), and the reaction is conducted in a tightly sealed container at 96-100° C. for 4-8 hours. The hydrazine and hydrazine sulfate are removed from the deacetylated product by dialysis and the product is dried by lyophilization. After treating with I$_2$ to convert the uronic acid hydrazides formed during hydrazinolysis to uronic acids, the resulting deacetylated heparin is subjected to periodate oxidation.

The periodate oxidation is performed in 0.01-0.1 M sodium periodate buffered to a pH of 3-6, preferably with 0.01-0.2 M sodium acetate or sodium phosphate buffer. Reaction mixtures containing commercially-available herparin/heparan sulfate at 0.5-10% (wt/volume) are incubated with the periodate oxidation solution at 0-37° C. in dark amber containers for 10% (wt/volume) are incubated with the periodate oxidation solution at 0-37° C. in dark amber containers for time intervals greater than 3 hours. While this temperature range is workable, lower temperatures are preferred, e.g., 0°-5° C., especially 0°-1° C. As would be expected, longer reaction times of e.g. 10–18 hours are preferred for lower temperatures. Excess periodate is then destroyed by addition of 50–300 mM ethylene glycol, and the reaction mixture is dialyzed against water.

Reduction is immediately effected with approximately 0.1–0.3 M, preferably about 0.2 M of a suitable aldehyde reducing agent, such as sodium borohydride at pH 8.0–9.0. Sodium bicarbonate buffer at approximately 0.2 M can appropriately be used to maintain this pH. It is important that the pH not be higher so that $\mu$-elimination is prevented. The concentration of the oxidized heparin in the reduction mixture is 1–4% (w/v). Excess borohydride is then destroyed by addition of concentrated HCl to approximately pH 3. The pH is then readjusted to neutrality with 2 M sodium carbonate and the product is desalted and dried.

The resulting composition contains modified but minimally-fragmented heparin/heparan sulfate of molecular weight in the range of 5-25 kd with an average chain length of 10-100 saccharide units. The composition is a mixture of deacetylation and oxidation products corresponding to the original mixture of glycosaminoglycans in the heparin/heparan sulfate preparation, but is free of other biological contaminants. The composition is useful therapeutically under circumstances where antiproliferative activity is desirable. In a typical preparation, the anticoagulant activity of the original heparin/heparan sulfate preparation is reduced to less than 5 U/mg, as opposed to 170 U/mg in the original preparation. The inhibition of smooth muscle cells by the preparation is the same as that of the original heparin on a weight basis.

LABELED FORMS OF THE INVENTION GLYCOSAMINOGLYCAN MIXTURES

The glycosaminoglycan mixtures of the invention can be provided with fluorescent, radioisotope, or enzyme labels as desired. Conventional techniques for coupling of label to carbohydrates or related moieties can be used. Such techniques are well established in the art. The labeled mixtures of the invention are useful in competitive immunoassays, as well as providing a means to trace the pharmacokinetics of the mixtures in vivo. Suitable radioisotope labels for this purpose include hydrogen[3], iodine[131], indium[111], technecium[99], and phosphorus[32]. Suitable enzymic labels include alkaline phosphatase, glucose-6-phosphate-dehydrogenase, and horseradish peroxidase. Particularly preferred fluorescent labels include fluorescein and dansyl. A wide variety of labels of all three types is known in the art.

PREPARATION OF ANTIBODIES

Antibodies may also be prepared to the glycosaminoglycan compositions of the invention. Typically, the components of the mixture are conjugated to suitable immunogenic carriers such as BSA, KLH, rotaviral protein VP6, and the like. Techniques for conjugation of carbohydrates to protein carriers are well known in the art and include, e.g., reductive amination and the use of bifunctional linkers such as those marketed by Pierce Chemical Company, Rockford, Illinois. The glycosaminoglycan components coupled to carriers are then administered to suitable mammalian host subjects using standard immunization protocols generally in the presence of adjuvants. Serum titers of the injected animals are periodically measured. Animals with high titers can be used as a source for antisera constituting polyclonal preparations immunoreactive with the glycosaminoglycan compositions of the invention.

If desired, monoclonal preparations may also be obtained by utilizing the antibody secreting cells of the immunized animals, including peripheral blood lymphocytes, but preferably spleen cells, and immortalizing these cells prior to screening the supernatants for immunoreactivity to the glycosaminoglycan composition. The cells may be immortalized using standard Kohler Millstein technology or by alternative methods such as infection with virus. The cell supernatants of the immortalized cell cultures are then screened using standard immunoassay technology for immunoreactivity with the glycosaminoglycan composition.

ADMINISTRATION AND USE

The glycosaminoglycan compositions of the invention are useful in therapeutic applications for treatment of conditions or diseases which are characterized by excessive and destructive smooth muscle cell proliferation. These conditions frequently occur where the subject has been exposed to trauma, such as in the case of surgical patients. The trauma caused by wounds or surgery results in vascular damage and secondary smooth muscle cell proliferation, which secondary proliferation results in vascular retinosis. This undesirable result can occur after vascular graft surgery, heart transplantation, balloon or laser angioplasty, arterial traumatic injury, postsurgical repair of muscular arteries, long-term in-dwelling of arterial catheters, invasive arterial diagnostic procedures, kidney, lung or liver transplants, coronary artery bypass surgery, carotid artery bypass surgery, femoral popliteal bypass surgery, and intracranial arterial bypass surgery.

In addition to secondary smooth muscle cell proliferation events occurring as a result of trauma, certain diseases are associated with unwanted vascular proliferation, although in these cases, too, it is assumed that some internal unknown injury has caused the secondary result. These disease states include Goodpasture syndrome, acute glomerulonephritis, neonatal pulmonary hypertension, asthma, congestive heart failure, adult pulmonary hypertension, and renal vascular hypertension.

For all these diseases and conditions, administration of suitable amounts of the compositions of the invention is useful in treatment. Administration is by typical routes appropriate for glycosaminoglycan compositions, and generally includes systemic administration, such as by injection. Particularly preferred is intravenous injection, as continuous injection over long time periods can be easily continued. Typical dosage ranges are in the range of 0.-10 mg/kg/hr on a constant basis over a period of 5-30, preferably 7-14, days. Particularly preferred dosage is about 0.3 mg/kg/hr, or, for a 70 kg adult, 21 mg/hr or 504 mg/day.

Other modes of administration are less preferred but may be more convenient. Injection subcutaneously at a lower dose or administered orally at a slightly higher dose than intravenous injection, or by transmembrane or transdermal or other topical administration for localized injury may also be effective. Localized administration through a continuous release device, such as a supporting matrix, perhaps included in a vascular graft material, is particularly useful where the location of the trauma is accessible.

Formulations suitable for the foregoing modes of administration are known in the art, and a suitable copendium of formulations is found in *Remington's Pharmaceutical Sciences*, Mack Publishing Company, Easton, Pa., latest edition.

The compositions of the invention may also be labeled using typical methods such as radiolabeling, fluorescent labeling, chromophores or enzymes, and used in a competitive assay for the amount of antiproliferative component in a biological sample. Suitable protocols for competitive assays of analytes in biological samples are well known in the art, and generally involve treatment of the sample, in admixture with the labeled competitor, with a specific binding partner which is reactive with the analyte such as, typically, an immunoglobulin or fragment thereof. The antibodies prepared according to the invention are useful for this purpose. The binding of analyte and competitor to the antibody can be measured by removing the bound complex and assaying either the complex or the supernatant for the label. The separation can be made more facile by preliminary conjugation of the specific binding partner to a solid support. Such techniques are well known in the art, and the protocols available for such competitive assays are too numerous and too well known to be set forth in detail here.

The antibodies of the invention are useful in immunoassays, not only of the type described above involving competition between labeled composition and the analyte antiproliferation factor in the sample, but also for direct immunoassay for the factor. Alternate protocols involving direct assays are also of wide variety and well known. Typically, the analyte bound to antibody is detected by means of an additional reactive partner which bears a label or other means of detection. Thus, in typical sandwich assays, for example, the binding of the antibodies of the invention to analyte can be detected by further reaction with a labeled preparation of these same antibodies or by labeled antibody immunoreactive with this preparation by virtue of species differences.

The antibodies of the invention can also be formulated into pharmaceutical compositions and used to stimulate the growth of smooth muscle cells in subjects for which this result is desirable.

ASSAYS FOR SMOOTH MUSCLE CELL PROLIFERATIVE INHIBITION

The glycosaminoglycan compositions are verified to inhibit smooth muscle cell proliferation using any standard assay for this activity. A convenient assay, in detail, is as follows:

Solutions to be tested are made up in "complete medium", which is DMEM medium containing 10% fetal calf serum and penicillin/streptomycin.

Bovine smooth muscle cells (SMC) are isolated from bovine aorta by the method of Ross, R., *J Cell Biol* (1971) 172-186. SMC from passage 3-10 are plated at 350-700 cells per well in 96-well microtiter plates in the medium above and allowed to attach for 2-4 hr. The complete medium is then replaced with DMEM supplemented with 0.1% fetal calf serum, and the cells are incubated for an additional period of about 24 to 72 hr to arrest cell growth. The low-serum medium is then replaced with complete medium containing the test samples.

The cells are allowed to grow for up to 7 days with replicate plates sampled at regular intervals. Cell number is determined by removing the medium and washing the cells with phosphate-buffered saline, adding 75-150 ul lysis buffer, and assaying for lactate dehydrogenase (LDH) activity, as described by Brandley, B., et al., *J Biol Chem* (1987) 262:6431. The activity of LDH is proportional to cell number.

Verification of the lack of anticoagulant activity is also conducted using standard assays. One such convenient assay shows a failure to bind to antithrombin-III. Other assays directly measure the lack of ability to inhibit blood clotting.

Antiproliferative activity is also shown in in vivo assays as follows: In an assay using inhibition of smooth muscle cell proliferation in the rat carotid denuded endothelium as an indicator, the glycosaminoglycan preparation can be delivered IV or using EVAC disks. In either case, rats, such as Sprague-Dawley albino rats weighing about 350 gm are anesthetized and the left common carotid artery is denuded of endothelium using a 2-F balloon embolectomy catheter.

For IV delivery, a catheter is immediately connected to a 2 ml 12/day osmotic pump (ALZA Corp.) which is inserted into the left jugular vein. For EVAC delivery, an EVAC disk containing the glycosaminoglycan is placed at the adventitial surface of the injured carotid artery. Control disks are used in some animals.

Fourteen days after surgery, the animals are again anesthetized and fixed by perfusion with 2.5% glutaraldehyde. Both ballooned and nonballooned arteries are excised and fixed in 10% formalin and examined by H & E staining. The common carotid arteries are evaluated by planimetric measurements (SigmaScan) for gross determination of smooth muscle cell proliferation into the tunica intima.

EXAMPLES

The following examples are intended to illustrate but not to limit the invention.

EXAMPLE 1

Preparation of NAC-Antiproliferative Heparin

Hydrazinolysis: Porcine mucosa heparin (50 mg of Ming Han heparin, 90020, 170 U/mg) was dissolved in distilled water to give 540 ml of a solution containing 80 g heparin. Eighteen g of hydrazine sulfate was dissolved in 1260 ml of anhydrous hydrazine in a 3 l beaker and the heparin solution was added to the beaker with moderate stirring. The temperature after mixing rose to 60° C. This reaction mixture, which contained 4 percent heparin and 1 percent hydrazine sulfate in a 70:30 mixture of hydrazine and water, was distributed equally into 8 Pierce 240 ml teflon containers. The containers were placed in an oven at 98° C. for 6 hours.

Isolation of the Deacetylated Polymer: The reaction vessels were cooled to room temperature and the solution of deacetylated heparin was transferred to dialysis tubing and dialyzed against four changes of distilled water (volume ratio of filtrate to water =1:10) using a 3500 molecular weight cut-off dialysis membrane. The dialyzed solution was concentrated to 1600 ml using a Pharmacia Tangential Flow Apparatus fitted with a Nova 1000 molecular weight cut-off membrane.

Conversion of Uronic Acid Hydrazides to Uronic Acid Residues: Sixteen g of $NaHCO_3$ was dissolved in the solution of the N-deacetylated heparin from above and 400 ml of a solution containing 0.2 M $I_2$ in 0.4 M KI was added. The oxidation was complete immediately, as indicated by the rapid bleaching of the I₂ color to a pale yellow (indicating the presence of excess I₂). The final pH of the solution was about 7. The product was dialyzed and concentrated as above to a final volume of 2800 ml.

Periodate Oxidation: The solution of the N-deacetylated heparin was transferred to an amber bottle; 200 ml of 4 M sodium acetate, pH 5.0, was added; and the mixture was chilled to 0° C. The oxidation was initiated by addition of 1000 ml of pre-chilled (0° C.) 0.2 M NaIO₄ to the solution of N-deacetylated heparin to give a final volume of 4 l. After 20 h at 0° C., the reaction mixture was warmed to room temperature and incubated with 16 ml ethylene glycol for 1 h to destroy excess periodate. This solution was filtered through Whatman No. 1 paper using a Buchner funnel. The filtrate was dialyzed and concentrated to 3000 ml using as described above.

Sodium Borohydride Reduction: The concentrated solution was chilled to 0° C. in an ice-water bath and 62.25 g of NaHCO₃ was added. A solution containing 28.35 g NaBH₄ in 750 ml of 0.05 M Na₂CO₃, prechilled to 0° C., was added to the reaction mixture and the reduction was allowed to proceed at 0° C with moderate stirring. The pH of the reaction mixture was 8.5 at the beginning of the reaction and rose to 9.5 as the reaction proceeded. After 2 h, the pH was adjusted to 4.0 by addition of 6 N HCl and the mixture was allowed to stand for 30 minutes at room temperature to destroy the excess NaBH₄. Finally, the pH was adjusted to 7.0. The product was dialyzed as described above and lyophilized to dryness. The overall yield was 60% of the starting weight of heparin.

For further purification, the product was dissolved in distilled water to give a 5 percent solution (wt/vol) and re-precipitated with 3 volumes of 99% ethanol. The precipitate was washed three times with 99% ethanol and the remaining ethanol was removed by placing the powder in the lyophilizer for 1 h.

EXAMPLE 2

Properties of the NAC-Antiproliferative Heoarin

The NAC-antiproliferative heparin prepared according to paragraph A of Example 1 shows less than 5 U/mg anticoagulant activity as compared to 170 U/mg for the starting material.

The NAC-antiproliferative heparin preparation of Example i was tested using intravenous delivery in the assay described hereinabove using 19 male Sprague-Dawley FBR albino rats weighing about 350 mg. The NAC-antiproliferative heparin was administered at 0.3 mg/kg/hour in lactated Ringer's solution to the 9 animals in the treatment group; lactated Ringer's solution alone was administered to the 10 animals in the control group. On the average, the lumen of the carotid artery in the animals in the control group was occluded to the extent of 36.9% of its cross sectional area (36.9% occlusion); the treatment showed 25.4% occlusion. Thus, the diminution in occlusion was significant, and could be optimized by prevention of the partial polymerization which occurred in this particular preparation. However, this study demonstrates that the NAC-antiproliferative heparin is effective in preventing myointimal hyperplasia.

In a similar study using EVAC disks containing 12 mg of the NAC-antiproliferative heparin prepared in Example 1, 19 male Sprague-Dawley rats were treated as described and administered 12 mg of the preparation in the EVAC disk. The control group containing 10 rats showed 43.4% occlusion; the 11 mg shown to be released from the EVAC implant resultsed in an 18.1% occlusion.

The NAC-antiproliferative heparins prepared in Example 1 were also analyzed for disaccharide composition by complete hydrolysis in the presence of nitrous acid, as described in Guo, Y., and Conrad, H. E., *Anal Biochem* (1989) 176:96–104. Hydrolysis with nitrous acid cleaves at N-sulfated glucosamine residues (but not at N-acylated glucosamine residue) and converts the reducing terminus to 2,5-anhydromannose. Subsequent reduction of this residue to 2,5-anhydromannitol is used to stabilize the cleavage products in this assay. The various hydrolysis products are quantitated relative to

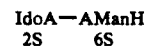

which is known not to be destroyed in periodate oxidation and is set at 100.

A comparison of the composition of the NAC-antiproliferative composition with that of heparin is shown in Table 1. "ND" represents not detectable. As shown in Table 1, disaccharide segments susceptible to periodate oxidation (i.e., those containing unsulfated IdoA or GlcA) are completely destroyed. Those units expected not to be susceptible to periodate oxidation (those containing 2S IdoA or 2S GlcA) are retained at approximately the same ratio to the resistant standard as their occurrence in heparin.

TABLE 1

| Disaccharide | Heparin | NAC-antiproliferative |
|---|---|---|
| IdoA—AManH or GlcA—AManH | 10.0 | ND |
| IdoA—AManH 2S | 18.0 | 20.0 |
| GlcA—AManH 6S | 18.6 | 0.5 |
| GlcA—AManH 2S | 2.6 | 2.6 |
| IdoA—AManH 6S | 12.9 | 0.5 |
| GlcA—AManH 3S,6S | 7.4 | 0.3 |
| IdoA—AManH 2S   6S | 100 | 100 |

As shown in Table 1, disaccharide units which contain susceptible non-sulfated IdoA or GlcA are greatly diminished from their content in heparin or are not detectable.

We claim:

1. A process to convert heparin to a deacetylated, oxidized, reduced heparin derivative that inhibits smooth muscle cell proliferation and substantially lacks anticoagulant activity, which process comprises:
   deacetylating N-acetylglucosamine(GlcNAc) of said heparin periadate;
   oxidizing the deacetylated heparin to effect complete conversion of gem-diols of iduronic and glucuronic acid that are not sulfated at either the 2or 3 positions of said acids, and gem $OH/NH_2$ of deacetylated GlcNAc to aldehydes;

reducing the aldehydes to alcohols without substantially fragmenting said deacetylated, oxidized treated heparin; and recovering the deacetylated, oxidized, reduced heparin derivative.

2. The process of claim 1 wherein said deacetylating step is conducted by treating said heparin with a reagent which comprises about 70% hydrazine (v/v) containing about 1% hydrazine sulfate in the presence of about 0.1-10% heparin at about 96°-100° C. for several hours; removing excess hydrazine; and treating the resultant with iodine.

3. The process of claim 1 wherein oxidizing said deacetylated heparin comprises combining in solution 0.5-10% deacetylated heparin (w/v) with 0.01-0.10 M periodate at pH3-6 at 0°-37° for a time sufficient to affect complete oxidation of said heparin by periodate.

4. The process of claim 3 wherein said reducing aldehydes to alcohols is conducted by treating the deacetylated periodate oxidized heparin with sodium borohydride at about 0.1-0.3 M and pH 8.9.

5. A non-coagulant, antiproliferative heparin derivative composition prepared by the process of claim 4.

6. A process to convert heparin to a composition comprising a heparin derivative capable of inhibiting smooth muscle proliferation but lacking anticoagulant properties, which process comprises:

treating said heparin with a reagent to effect deacetylation of said heparin;

incubating a solution containing 0.5-10% deacetylated heparin (w/v), 0.01-0.1 M periodate, and pH 3-6 at 0°C.-37° C. for a time sufficient to effect complete conversion of gem-diols and gem $OH/NH_2$ to aldehydes in said heparin by periodate;

removing excess periodate;

removing salt to obtain a salt-free resultant;

treating the resultant with reducing agent effective to convert substantially all aldehyde moieties to alcohol moieties under conditions wherein fragmentation of said heparin derivative is inhibited; and recovering said unfragmented heparin derivative.

7. The process of claim 6 wherein said deacetylating step is conducted by treating said heparin with a reagent which comprises about 70% hydrazine (v/v) containing about 1% hydrazine sulfate in the presence of about 0.1-10% heparin at 96°-100° C. for several hours; removing excess hydrazine; and treating the resultant with iodine.

8. The process of claim 6 wherein said reducing is conducted by treating the deacetylated oxidized heparin with sodium borohydride at about 0.1-0.3 M and pH 8-9.

9. A pharmaceutical formulation comprising the non-anticoagulant, antiproliferative heparin derivative composition of claim 5 and a pharmaceutically acceptable excipient.

10. A method to treat disease in a patient resulting from smooth muscle cell proliferation, which method comprises administering to a patient in need of such treatment an effective amount of the heparin derivative composition of claim 5 or a pharmaceutical composition thereof to treat said disease.

* * * * *

UNITED STATES PATENT AND TRADEMARK OFFICE
CERTIFICATE OF CORRECTION

PATENT NO. : 5,250,519
DATED : October 5, 1993
INVENTOR(S) : H. Edward Conrad and Yuchuan Guo It is certified that error appears in the above-indentified patent and that said Letters Patent is hereby corrected as shown below:

In Col. 6, line 63, delete "herparin" and insert --heparin--.

In Col. 7, line 13, delete "μ-elimination" and insert --β-elimination--.

In Col. 8, line 28, delete "retinosis" and insert --restenosis--.

In Col. 12, line 66, delete "periadate".

In Col. 12, line 67, before "oxidizing" insert --periodate--.

Signed and Sealed this

Twenty-fifth Day of October, 1994

Attest:

BRUCE LEHMAN

Attesting Officer     Commissioner of Patents and Trademarks